(12) United States Patent
Goldfine et al.

(10) Patent No.: US 7,528,598 B2
(45) Date of Patent: May 5, 2009

(54) FASTENER AND FITTING BASED SENSING METHODS

(75) Inventors: Neil J. Goldfine, Newton, MA (US); David C. Grundy, Reading, MA (US); Andrew P. Washabaugh, Chula Vista, CA (US); Yanko K. Sheiretov, Waltham, MA (US); Darrell E. Schlicker, Watertown, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 219 days.

(21) Appl. No.: 11/473,297

(22) Filed: Jun. 22, 2006

(65) Prior Publication Data

US 2007/0007955 A1 Jan. 11, 2007

Related U.S. Application Data

(60) Provisional application No. 60/693,347, filed on Jun. 22, 2005, provisional application No. 60/696,625, filed on Jul. 5, 2005.

(51) Int. Cl.
*G01R 33/12* (2006.01)
*G01R 27/26* (2006.01)

(52) U.S. Cl. .................. 324/240; 324/242; 324/659

(58) Field of Classification Search ................. 324/202, 324/222, 227, 228, 232, 234, 238, 239, 240, 324/241, 242, 243, 658, 659, 663, 691
See application file for complete search history.

(56) References Cited

U.S. PATENT DOCUMENTS

| | | | |
|---|---|---|---|
| 3,665,756 A | 5/1972 | Russell | |
| 3,977,236 A | 8/1976 | Raatz et al. | |
| 4,095,181 A | 6/1978 | Harris | |

(Continued)

OTHER PUBLICATIONS

Bowler, N., "Theory of Four-Point Direct-Current Potential Drop Measurements on a Metal Plate," Research in Nondestructive Evaluation, vol. 17, pp. 29-48, (2006).

(Continued)

*Primary Examiner*—Kenneth J Whittington
(74) *Attorney, Agent, or Firm*—Hamilton, Brook, Smith & Reynolds, P.C.

(57) ABSTRACT

Damage and usage conditions in the vicinity of fasteners in joined structures are nondestructively evaluated using the fasteners themselves. Sensors or sensor conductors are embedded in the fasteners or integrated within the fastener construct, either in the clearance gap between the fastener and the structure material or as an insert inside the shaft or pin of the fastener. The response of the material to an interrogating magnetic or electric field is then measured with drive and sense electrodes both incorporated into the fastener or with either drive or sense electrodes external to the fastener on the material surface. In another configuration, an electric current is applied to one or more fasteners and the electric potential is measured at locations typically between the driven electrodes applying the current. The potential is measured circumferentially around the fastener at locations on the material surface or across pairs of fasteners throughout or along the joint. The voltage or potential measurement electrodes may be collinear with the drive electrodes. State sensitive material layers can be added either to the fastener or the test material layers in order to enhance observability of the test material condition, such as the presence of a crack, mechanical stress, delamination, or disbond.

33 Claims, 8 Drawing Sheets

U.S. PATENT DOCUMENTS

| | | | |
|---|---|---|---|
| 4,142,154 | A | 2/1979 | Couchman |
| 4,203,069 | A | 5/1980 | Davis |
| 4,247,819 | A | 1/1981 | Shimada et al. |
| 4,383,218 | A | 5/1983 | Hansen |
| 4,454,790 | A | 6/1984 | Rieben |
| 4,528,856 | A | 7/1985 | Junker |
| 4,706,020 | A | 11/1987 | Viertl et al. |
| 4,814,690 | A | 3/1989 | Melcher et al. |
| 4,823,606 | A | 4/1989 | Malicki |
| 4,846,001 | A | 7/1989 | Kibblewhite |
| 5,015,951 | A | 5/1991 | Melcher |
| 5,023,549 | A | 6/1991 | Dau et al. |
| 5,047,719 | A | 9/1991 | Johnson et al. |
| 5,156,636 | A | 10/1992 | Kuljis |
| 5,291,789 | A | 3/1994 | Walton |
| 5,399,968 | A | 3/1995 | Sheppard et al. |
| 5,453,689 | A | 9/1995 | Goldfine et al. |
| 5,499,540 | A | 3/1996 | Whaley et al. |
| 5,510,709 | A | 4/1996 | Hurley et al. |
| 5,549,803 | A | 8/1996 | Schoess et al. |
| 5,610,515 | A | 3/1997 | Soules |
| 5,648,721 | A | 7/1997 | Wincheski et al. |
| 5,675,087 | A | 10/1997 | MacLauchlan |
| 5,739,686 | A | 4/1998 | Naughton et al. |
| 5,793,206 | A | 8/1998 | Goldfine et al. |
| RE36,986 | E | 12/2000 | Melcher |
| 6,188,218 | B1 | 2/2001 | Goldfine et al. |
| 6,380,747 | B1 | 4/2002 | Goldfine et al. |
| 6,479,989 | B2 | 11/2002 | Taylor |
| 6,486,673 | B1 | 11/2002 | Goldfine et al. |
| 6,545,469 | B1 | 4/2003 | Batzinger et al. |
| 6,657,429 | B1 | 12/2003 | Goldfine et al. |
| 6,727,690 | B2 | 4/2004 | Soules |
| 6,727,691 | B2 | 4/2004 | Goldfine et al. |
| 6,781,387 | B2 | 8/2004 | Goldfine et al. |
| 6,784,662 | B2 | 8/2004 | Schlicker et al. |
| 6,888,346 | B2 | 5/2005 | Wincheski et al. |
| 6,952,095 | B1 | 10/2005 | Goldfine et al. |
| 6,992,482 | B2 | 1/2006 | Shay et al. |
| 2001/0054896 | A1 | 12/2001 | Mednikov et al. |
| 2002/0075006 | A1 | 6/2002 | Goldfine et al. |
| 2002/0163333 | A1 | 11/2002 | Schlicker et al. |
| 2003/0071614 | A1 | 4/2003 | Buttle |
| 2003/0071615 | A1 | 4/2003 | Schlicker et al. |
| 2003/0173958 | A1 | 9/2003 | Goldfine et al. |
| 2004/0100277 | A1 | 5/2004 | Tam |
| 2004/0124833 | A1 | 7/2004 | Kliman et al. |
| 2005/0007106 | A1 | 1/2005 | Goldfine et al. |
| 2005/0083032 | A1 | 4/2005 | Goldfine et al. |
| 2008/0258720 | A1 | 10/2008 | Goldfine et al. |

OTHER PUBLICATIONS

Navy Phase I Proposal, titled "In-situ projected field and near surface sensors for direct condition monitoring of engine hot section components," Topic #N06-T011, dated Apr. 13, 2006.

Auld, B.A. and Moulder, J.C. (1999), "Review of Advances in Quantitative Eddy-Current Nondestructive Evaluation," Journal of Nondestructive Evaluation, vol. 18, No. 1.

Bozorth, R.M., Ferromagnetism, IEEE Press, 1978.

Bray, D.E., ed., Residual Stress Measurement and General Nondestructive Evaluation, PVP-vol. 429, ASME Pressure Vessels and Piping Conference, Atlanta, GA, ASME, 2001.

Hydrogen in Metals, Proceedings of the Second Japan Institute of Metals, International Symposium, 1979.

Interrante, C. and Pressouyre, G. "Current Solutions to Hydrogen Problems in Steels," Proceedings of the First International Conference, ASM, 1982.

Lawrence, S.C. "Hydrogen Detection Gage," Hydrogen Embrittlement Testing, ASTM STP 543, 1974, pp. 83-105.

Navy Phase I Proposal, titled "Wireless Communications with Electromagnetic Sensor Networks for Nondestructive Evaluation," Topic #N01-174, dated Aug. 13, 2001.

Air Force Phase I Proposal, titled "Three-Dimensional Magnetic Imaging of Damage in Multiple Layer Aircraft Structures," Topic #AF02-281, dated Jan. 14, 2002.

DOE Phase II Proposal, titled "Intelligent Probes for Enhanced Non-Destructive Determination of Degradation in Hot-Gas-Path Components," Topic #44c, dated Mar. 23, 2002.

Air Force Phase II Proposal, titled "Detection and Imaging of Damage, Including Hydrogen Embrittlement Effects in Landing Gear and Other High-Strength Steel Components," Topic #AF01-308, dated Apr. 9, 2002.

Strategic Environmental Research and Development Program Proposal, titled "High Resolution Inductive Sensor Arrays for UXO Detection, Identification and Clutter Suppression," SON #UXSON-02-03, dated Apr. 17, 2002.

NASA Phase II Proposal, titled "Shaped Field Giant Magnetoresistive Sensor Arrays for Materials Testing," Topic #01-11 A1.05-8767, dated May 2, 2002.

Navy Phase I Proposal, titled "Observability Enhancement and Uncertainty Mitigation for Engine Rotating Component PHM," Topic #N02-188, dated Aug. 14, 2002.

NASA Phase I Proposal, titled "Non-Destructive Evaluation, Health Monitoring and Life Determination of Aerospace Vehicles/Systems," Topic #02-H5.03-8767, dated Aug. 21, 2002.

Final Report submitted to FAA, titled "Crack Detection Capability Comparison of JENTEK MWM-Array and GE Eddy-current Sensors on Titanium ENSIP Plates", dated Sep. 28, 2001, Contract #DTFA03-00-C-00026, option 2 CLIN006 and 006a.

Final Report submitted to FAA, titled "Aircraft Hidden Damage Detection and Assessment with Conformable Eddy Current Arrays," FAA Contract DTFA03-01-C-00024, dated Mar. 29, 2002.

Final Report submitted to NASA, titled "Shaped Field Giant Magnetoresistive Sensor Arrays for Materials Testing," dated May 3, 2002.

Final Report submitted to Air Force, titled "Detection and Imaging of Damage, Including Hydrogen Embrittlement Effects in Landing Gear and Other High-Strength Steel Components," dated Jul. 3, 2002.

Final Report submitted to Navy, titled "Wireless Communications with Electronic Sensor Networks for Nondestructive Evaluation," dated Jul. 15, 2002.

Final Report titled "Portable Accumulated Fatigue Damage Inspection System Using Permanently Mounted and Wide-Area Imaging MWM-Arrays," dated Aug. 23, 2002.

Technical paper titled "MWM Eddy-Current Arrays for Crack Initiation and Growth Monitoring," submitted to International Journal of Fatigue, from the International Conference on Fatigue Damage of Structural Materials IV, Hyannis, MA, 2002.

Technical paper titled "Conformable Eddy-Current Sensors and Arrays for Fleetwide Gas Turbine Component Quality Assessment," published in ASME Journal of Engineering for Gas Turbines and Power, vol. 124, No. 4, pp. 904-909; Oct. 2002.

Technical paper titled "Residual and Applied Stress Estimation from Directional Magnetic Permeability Measurements with MWM Sensors," published in ASME Journal of Pressure Vessel Technology, vol. 124, pp. 375-381; Aug. 2002.

Technical paper titled "Fatigue and Stress Monitoring Using Scanning and Permanently Mounted MWM-Arrays," presented at 29th Annual Review of Progress in QNDE; Bellingham, Washington; Jul. 2002.

Technical paper titled "Absolute Electrical Property Imaging using High Resolution Inductive, Magnetoresistive and Capacitive Sensor Arrays for Materials Characterization," presented at 11th International Symposium on Nondestructive Characterization of Materials, Berlin, Germany; Jun. 2002.

Technical paper titled "Application of MWM® Eddy-Current Technology during Production of Coated Gas Turbine Components," presented at 11th International Symposium on Nondestructive Characterization of Materials, Berlin, Germany; Jun. 2002.

Technical paper titled "Friction Stir Weld Inspection through Conductivity Imaging using Shaped Field MWM® -Arrays," presented at ASM Trends in Welding Conference, Callaway Gardens, GA; Apr. 2002.

Technical paper and presentation slides, titled "MWM-Array Characterization and Imaging of Combustion Turbine Components," presented at EPRI International Conference on Advances in Life Assessment and Optimization of Fossil Power Plants, Orlando, FL; Mar. 2002.

Technical paper titled "Surface Mounted and Scanning Periodic Field Eddy-Current Sensors for Structural Health Monitoring", presented at the IEEE Aerospace Conference, Mar. 2002.

Presentation slides titled "Corrosion Detection and Prioritization Using Scanning and Permanently Mountable MWM Eddy-Current Arrays," U.S. Army Corrosion Summit, Mar. 2002.

Technical paper and presentation slides titled "Shaped-Field Eddy-current Sensors and Arrays", SPIE 7th Annual International Symposium: NDE for Health Monitoring and Diagnostics, Mar. 2002.

Technical paper titled "Corrosion Detection and Prioritization Using Scanning and Permanently Mounted MWM Eddy-Current Arrays", Tri-Service Corrosion Conference, Jan. 2002.

Technical presentation slides "Condition Assessment of Engine Component Materials Using MWM Eddy-Current Sensors," ASNT Fall Conference, Columbus, OH; Oct. 2001.

Technical paper titled "Flexible Eddy Current Sensors and Scanning Arrays for Inspection of Steel and Alloy Components," 7th EPRI Steam Turbine/Generator Workshop and Vendor Exposition, Baltimore, MD; Aug. 2001.

Technical paper titled "Applications for Conformable Eddy Current Sensors including High Resolution and Deep Penetration Sensor Arrays in Manufacturing and Power Generation," ASME 7th NDE Topical Conference, San Antonio, Texas; 2001.

Technical paper titled "*MWM Eddy Current Sensor Array Imaging of Surface and Hidden Corrosion for Improved Fleet Readiness and Cost Avoidance*," presented at U.S. Army Corrosion Conference, Clearwater Beach; FL, Feb. 11-13, 2003.

Technical paper titled "*MWM Eddy Current Sensor Array Characterization of Aging Structures Including Hidden Damage Imaging*," presented to the Aerospace Committee, NACE Conference, San Diego; CA, Mar. 17-19, 2003.

Air Force Phase II Proposal, titled "Three Dimensional Magnetic Imaging of Damage in Multiple Layer Aircraft Structures," Topic #AF02-281, dated Feb. 20, 2003.

FASTENER AND FITTING BASED SENSING METHODS

RELATED APPLICATIONS

This application claims the benefit of U.S. Provisional Application No. 60/693,347 filed on Jun. 22, 2005 and U.S. Provisional Application Ser. No. 60/696,625 filed on Jul. 5, 2005. The entire teachings of the above applications are incorporated herein by reference.

BACKGROUND OF THE INVENTION

The technical field of this invention is that of nondestructive materials characterization, particularly damage detection and monitoring using sensors.

In some situations, such as on aircraft, the component material of interest has multiple layers and these layers are joined or clamped together by one or more fasteners. These fasteners can have a variety of geometries, but in many situations are threaded or press-fit into the holes in the material layers. When using these fasteners, problems include inconsistency in the clamp-up, preloading of the fasteners and lack-of-grip tolerance, as well as damage in the form of galling between the nut and bolt or damage at the load bearing surface. These variations in fastener installation and damage eventually resulting from usage can lead to reduced aircraft life and substantial inspection and rework costs. Inspections are commonly performed to evaluate the condition of the material near the fastener, but the variability in fastener properties or even the differences in properties between fasteners and the adjacent structural or joined material can mask the response of a crack or other damage to the material itself. One common nondestructive testing method, call bolt-hole eddy current testing (ET), requires the removal of the fastener (by "drilling out") to perform the inspection.

Another common inspection and nondestructive characterization technique for the inspection of damage around fasteners, termed conventional eddy-current sensing involves the excitation of a conducting winding, the primary, with an electric current source of prescribed frequency. This produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks, without removing the fastener. A particular difficulty with eddy-current sensors is the effect of material discontinuities, such as edges of the material for detecting cracks around fasteners. These edges and fasteners can strongly influence the response of the sensor and potentially mask the response of cracks that commonly form at these material discontinuities.

An example of such an eddy-current technique is in U.S. Pat. No. 5,399,968. In this patent, Sheppard, et al. teaches of eddy-current probes for the inspection of cracks or flaws in multi-layered structures. Circular and rectangular probe designs are disclosed, with one or two drive winding coils and arrays of sensing element coils. The probes also use a ferrite core for creating a magnetic circuit that guides the magnetic flux into the test material. U.S. Pat. No. 6,952,095 teaches of the use of surface mounted sensors being mounted near and around fasteners for the inspection of damage.

Spatially periodic field eddy-current sensors have also been developed for material condition assessment. For example U.S. Pat. Nos. 5,015,951 and 5,453,689 described flexible eddy-current sensors that have been used to measure foil thickness, characterize coatings, and measure porosity, as well as to measure property profiles as a function of depth into a component material. Sensor arrays have also been developed, as described for example in U.S. Pat. Nos. 5,793,206, 6,657,429, and 6,784,662.

SUMMARY OF THE INVENTION

Aspects of the methods described herein involve nondestructive evaluation of joined materials for monitoring of material condition, usage, and damage in the vicinity of the fasteners used for joining the materials. In one embodiment, the test material is monitored by using a fastener that has sensor conductors embedded or integrated into the fastener structure, with one of the sensor conductors driven by an electric signal to create an interrogating field and with the response of another sensor conductor used to assess the material condition.

In an embodiment, an embedded conductor is driven with a current and a voltage is measured on a second conductor. The electrical connections to the fastener may be made through the head or the nut of the fastener.

In another embodiment, a state sensitive indicator layer is used with the sensor conductors to enhance the sensitivity to the material condition, such as a magnetically permeable material whose permeability varies with the temperature or stress of the test material. In embodiments, the interrogating field is a magnetic field or an electric field.

In another embodiment, the test material is joined by multiple fasteners and the fasteners themselves are used as part of the examination process. For example, probe contacts can be made to two of the fastener so that an electrical current can be driven or injected between the fasteners with a voltage response then measured. This voltage may be made by probe contacts to the fasteners in the test material, such as the fasteners used to drive the electrical signal or other fasteners positioned between the driven fasteners. This voltage can then be used to assess the material condition. In an embodiment, the driven and voltage sensing fasteners are collinear. In another embodiment, the voltage is measured with a conducting contact at the test material surface, possibly with multiple contacts and at multiple locations along the surface.

In other embodiments, the voltage is measured with a non-contact, capacitive sensor or with a magnetic field sensor such as a wound coil or a magnetoresistive sensor.

In a particular embodiment, the fasteners are in electrical contact with the test material layers. In another embodiment, the fasteners are electrically isolated from the test material, for example a conducting fiber composite, and the opposite side of the test material has a cross-connection between at least two of the fasteners, such as a spar or rib of an aircraft, so that the injected current can travel relatively deeply into the structure. In embodiments, the cross-connection provides a pathway for magnetic flux or electric current.

In an embodiment, the state of a test material is by using a fastener that has an integrated or embedded drive conductor which is used to impose a magnetic field in the test material, measuring a response of a sense conductor near the test material, and using this response to determine the test material state. Representative states include stress, the presence of a crack, cumulative damage, and the temperature of the test material.

In an embodiment, the sensor conductor is also integrated into the construction of the fastener to more easily permit installation with the fastener in the structure. In another embodiment, multiple sense conductors having the form of single loops are placed circumferentially around the fastener on the surface of the test material.

In yet another embodiment, the fastener has a channel, such as a cylindrical groove down its center, which permits access to electrical contacts for the conductors. These contacts can be accessed with a connector that is inserted into the head or bottom of the fastener. The contacts may be to wound coils, such as a solenoid coil that passes around the fastener shaft or to contact points that allow current to be injected and voltages to be measured along the length of the fastener.

In an embodiment, the fastener also contains a state sensitive or indicator material layer. This layer may be in the form of a coating or a sleeve, such as a bushing. A sleeve placed around the outside of the fastener could be used for protection of the conductors and can help to provide relatively uniform surface contact between the fastener and the test material. Also, the conductors themselves can be manufactured with a deposition process, where an insulating layer is first placed on the fastener and then the conductor layers are deposited. Additional insulating layers can be placed over the surface to provide additional protection or insulation as necessary.

A method is discussed for monitoring and detecting the state of a test material around a fastener. The method comprises mounting a fastener into a test material, with the fastener having an integrated drive conductor. The conductors are driven with an electric signal to create an interrogating field within the test material. The interrogating field may be electric or magnetic. A response is measured with at least one other conductor to measure the test material and determine its state. The state of the material may be stress, damage in the form of a crack, or temperature, and a correlation between a sense conductor response and stress may be obtained. The correlation may be used to determine the stress from the response.

The fastener may further comprise an indicator layer that enhances sensitivity to the test material condition. Electrical connections to the conductor may be made through the head of the fastener. The fastener may comprise a channel to provide access to at least one conductor integrated into the fastener, and inserting a connector into the channel to contact a conductor. The channel may be in the form of a cylindrical hole and the connector may have the form of a cylindrical plug that can be inserted into the fastener from one side. The fastener may also have a sensitive material layer, which may be in the form of a coating that enhances the sensitivity of the response to the state of interest. The sensitive material may have an electrical property that varies with cumulative damage. The fastener may be in an aircraft.

Multiple sense conductors, each having the form of a simple loop, may be placed in a circumferential configuration along a surface of the test material outside of the fastener hole, with a voltage across each sensor conductor is measured. At least one sense conductor may be integrated into the fastener, with the fastener and conductors forming a single construct for ease of installation. The sense conductor may be in the form of a washer.

The method may also comprise applying an electrical current between the fastener and a location remote from the fastener, and measuring a voltage response. The remote location may be another fastener. The voltage may be used to access a condition of the test material. The fasteners used for measuring the voltage are between fasteners used for applying the electric current. The fasteners used for measuring the voltage may also be the same as the fasteners used for applying the electric current. The fasteners may also be electrically isolated from the material layers and the opposite side of the material layers from which the current is injected has a cross-connection between the fasteners. The cross-connection may provide a continuity of magnetic flux or an electrical continuity.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

A description of preferred embodiments of the invention follows.

This invention addresses the need for enhanced monitoring of damage and usage states of materials, as well as material conditions resulting for example from processing during manufacture. This includes monitoring of damage, usage and material conditions during in-service use or processing, as well as scheduled or opportunistic inspection/sensing during down-time. Scheduled or opportunistic sensing might also be associated with specific naturally occurring states of the system or actuated states, such as temperature, load, or other measurable or controllable variables. The specific implementation addressed here is the use of sensors or sensor conductors embedded into fasteners, bushings, washers and fittings or other means and elements used for joining materials. Such joints tend to have two features: (1) load transfer or transfer of energy in some other form, such as thermal, and (2) enhanced access and modularity that enables insertion of sensors or access to sensor connectors either directly (e.g., with electrical wires) or indirectly through some other means of energy transfer or communication. These embedded sensors can be used for cradle to grave monitoring, through the manufacturing process for intermediate states during processing and even quality assessment, then for in-service monitoring and finally for rework, repair and even retirement/recycling monitoring. The goal of this lift-cycle monitoring is enhanced functional performance and total ownership cost reduction.

For the embedded sensors, one or more sensor conductors are embedded into the fasteners themselves or integrated within the fastener construct so that the field used to interrogate the test material can penetrate more readily into the areas of interest for the examination. In similar embodiments, one or more sensor electrodes or conductors are embedded into the test material itself. In another embodiment, electrical connections are made to the fasteners and the fasteners are used essentially as probes for monitoring the properties of the joined material. In many cases, the property of interest in the joined material is the presence and even size of cracks, but in other cases the applied load or residual stress in the material is of interest.

Figure 1:
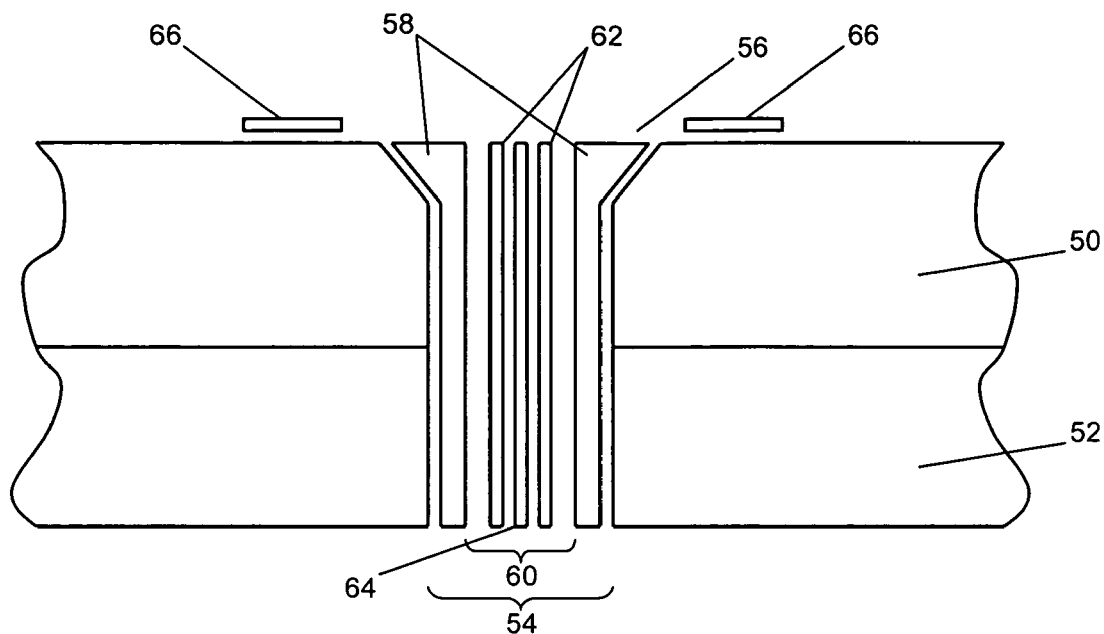
FIG. 1 shows a schematic diagram of a sensor sleeve embedded inside a fastener.

As an example of modified fastener geometry suitable for monitoring of the test material condition, consider FIG. 1. In this case, test material layers 50 and 52 are joined by a fastener 56. To accommodate the fastener, a hole 54 is formed in the test material. The hole size relative to the diameter of the fastener depends upon the type of fastener to be used, such as a threaded fastener, interference fit, flush-mounted head, or raised-head. In FIG. 1, a flush-mounted fastener head is shown. The fastener has an outer section 58 with a central hole 60 through which a sleeve 62 is inserted. The sleeve contains a sensor, sensor conductors, and possibly an indicator or state sensitive material that enhances sensor sensitivity to the properties of the test material or to applied loads. The sleeve 62 is typically mounted on an insert 64 for additional structural support. Representative materials include aluminum or titanium alloys or graphite fiber composites for the test material layers, titanium or aluminum for the fastener material, and carbon fiber graphite for the insert 64. Representative state sensitive materials include nickel-based alloys, cobalt and cobalt-based alloys.

In operation, the sleeve 62 can be press-fit into the hole 60 in the fastener so that the sensor or sensor conductors are effectively embedded within the fastener structure. Note that the sensors can be monitored during the press fit or other installation operation in order to monitor stress or geometric features during insertion and joint assembly. The press fit results in minimal gaps between the sleeve and the fastener sections 58. Leads to the sensor conductors are preferably passed through the bottom of the fastener, for example into the interior of an aircraft, but may also pass through the fastener head. In an embodiment, a sealant groove or similar slot is used to channel the leads to an accessible location. An electric signal is applied to sensor electrical conductors on the sleeve or at the surface of the test material to create an interrogating field in the test material. Note that 66 in FIG. 1 indicates sensor conductors placed at the surface of the test material. The response of the test material is then detected with additional sensor electrical conductors, from which one or more test material properties can be determined. In this format, the driven and sense conductors can both be embedded in the fastener, the drive can be embedded with the sense element (or elements) placed at the surface, or the sense elements can be embedded with the drive at the surface.

When one of the sensor conductors (either the drive or sense element) is placed externally on the material surface, the surface sensor conductors can be scanned to possibly improve the sensitivity to hidden material condition. The external conductors may be scanned simply in a linear path, or it may follow the contour of any features in the test material, such as in a circular path around the fastener or in other non-circular contours. Alternatively, the external sensors can remain stationary and be monitored continuously, periodically or opportunistically.

Figure 2:
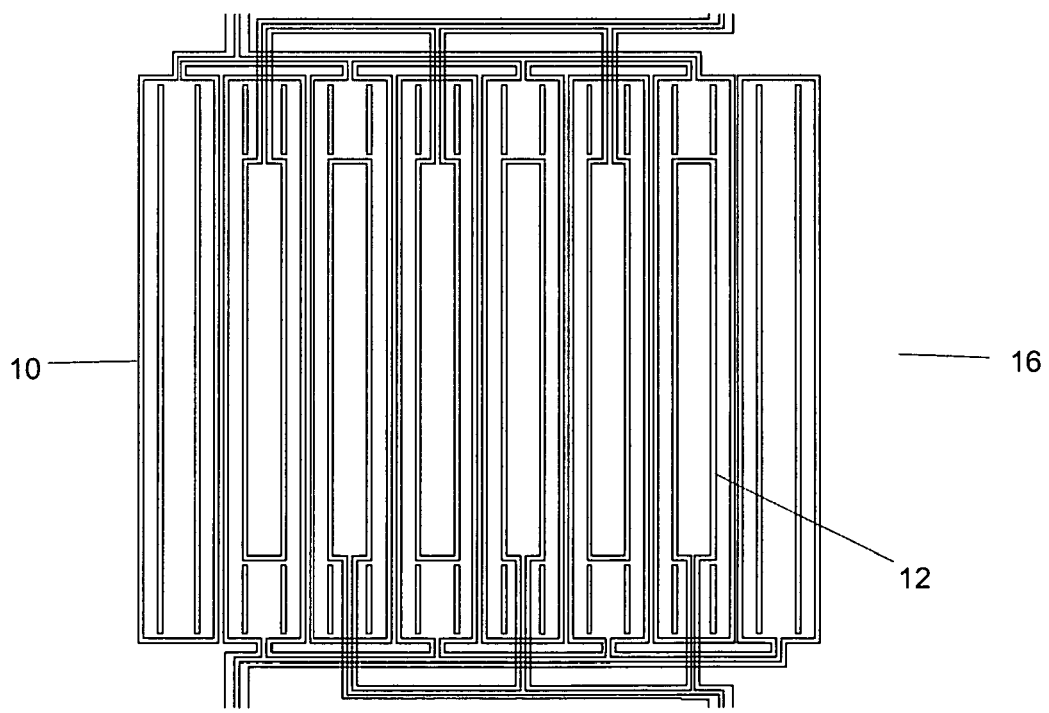
FIG. 2 shows a drawing of a spatially periodic field eddy-current sensor.

An example magnetic field based sensor that operates in the magnetoquasistatic regime and is well-suited to this approach is shown in FIG. 2. This meandering winding magnetometer (MWM®) is a "planar," conformable eddy-current sensor that was designed to support quantitative and autonomous data interpretation methods. The sensor 16 is described in U.S. Pat. Nos. 5,453,689, 5,793,206, 6,188,218, and 6,657, 429. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength λ. A current is applied to the primary winding to create a magnetic field and the response of the test material to the magnetic field is determined through the voltage measured at the terminals of the secondary windings. This geometry creates a magnetic field distribution similar to that of a single meandering primary winding. A single element sensor has all of the sensing elements connected together. The net magnetic vector potential produced by the current in the primary can be accurately modeled as a Fourier series summation of spatial sinusoids, with the dominant mode having the spatial wavelength λ. For an MWM-Array, the responses from individual or combinations of the secondary windings can be used to provide a plurality of sense signals for a single primary winding construct as described in U.S. Pat. No. 5,793,206 and Re. 36,986.

Figure 3:
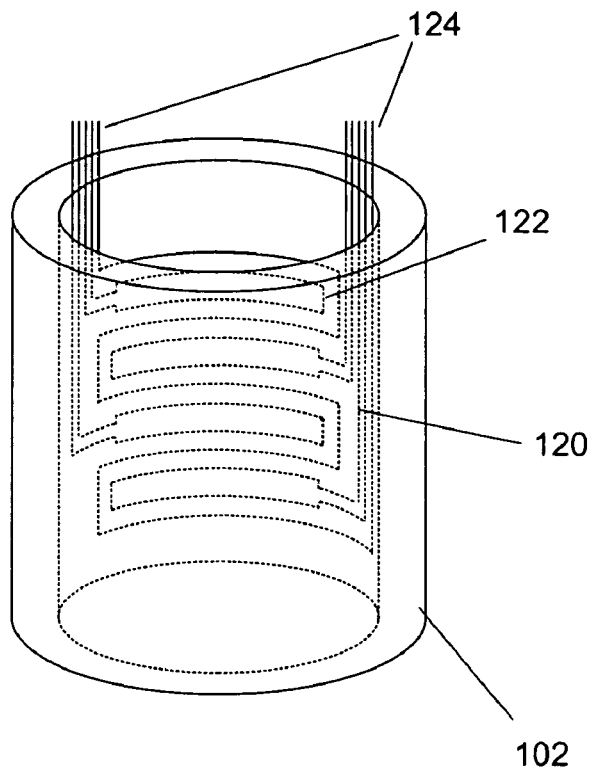
FIG. 3 shows an illustration of an MWM-Array inside a hollow fastener.
Figure 15:
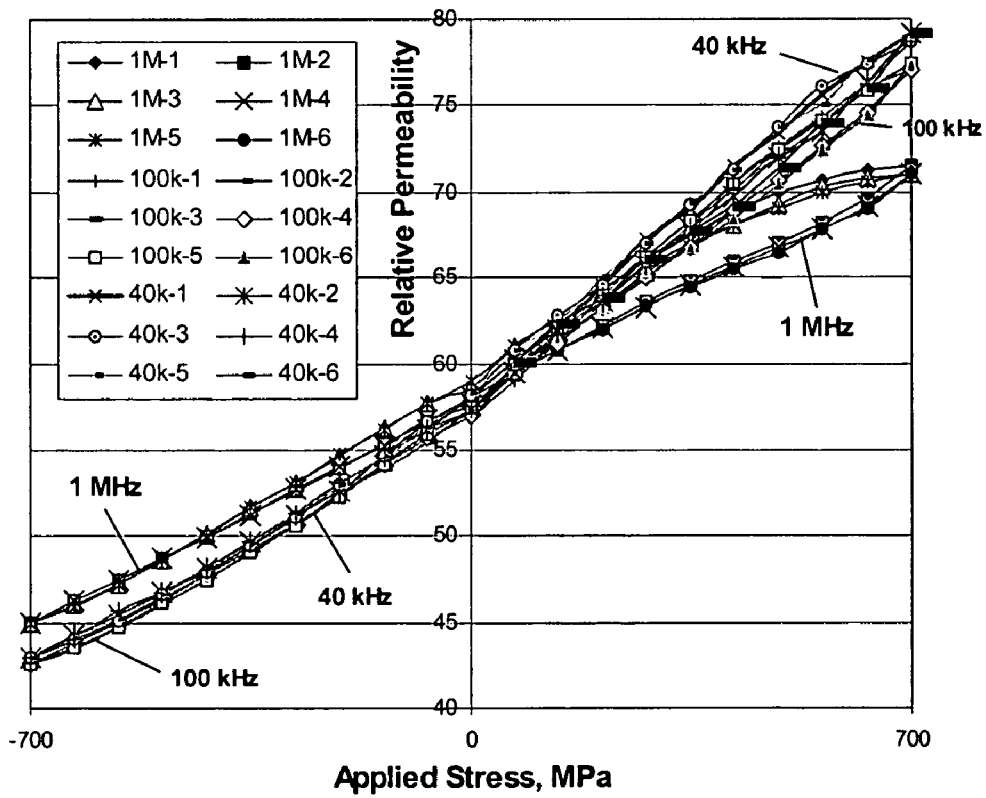
FIG. 15 shows the magnetic permeability variation with bending stress in a shot-peened high-strength steel specimen.

FIG. 3 shows an example geometry where a sensor array is mounted inside a cylindrical hole, possibly inside a fastener or inside a sheath the goes over the pin of the fastener or is itself inserted into the fastener. This type of fastener may be used, for example, in structures where a sealant or lubricant needs to be injected. Monitoring the properties of the fastener itself can provide load information in fatigue test articles and structures as described in U.S. patent application Ser. No. 10/351,978, filed on Jan. 24, 2003, the entire teachings of which are incorporated herein by reference. In the load sensing application, an eddy-current sensor array 120 is mounted inside the hollow fastener 112 and monitors changes in the fastener material properties as the load and stress distribution changes. For example, one or more property based parameters that relate to stresses can be measured. The use of a sensor array that has multiple sensing elements 122 with individual sensing element leads 124 permits the properties along the length of the fastener and/or around the circumference of the fastener to be monitored. In one embodiment, one parameter can be permeability in the axial direction and the other parameter can be permeability in the circumferential direction. Then, permeability changes can be related to stresses in the fasteners. In embodiments, a stress sensitive coating or a press fit bushing with a stress sensitivity electrical property, such as magnetic permeability, is added. This stress sensitive coating may be on the fastener or on the internal diameter of the hole or the external or internal diameter of the bushing. As an example, FIG. 15 shows the magnetic permeability variation with applied stress for a shot-peened magnetizable steel at several excitation frequencies. Similar plots or correlation curves can be generated for electrical property variations with temperature or even cumulative fatigue damage.

In the present invention, instead of monitoring the properties of the fastener, the sensor or sensor array is used to monitor the properties of the test material or state sensitive layer adjacent to the fastener, potentially for crack initiation and growth, to detect cracks, or to assess fastened load or damage dependent electrical material properties. This is achieved by configurations that allow significant portions of the interrogating field, such as a magnetic field, to penetrate into the regions of interest in the test material. With sensor conductors embedded or integrated with the fastener construction, low frequency operation and high signal currents can be used so that the magnetic field can penetrate through the fastener material into the test material. An advantage of this approach, particularly when the embedded conductor is used as the drive conductor, is that the distance between the region of interest in the test material, such as the interface area between two material layers where cracks are likely to form, is much smaller than the distance to the material surface from which a conventional sensor would be used to examine the test material. Also, the positions of the sensor conductors can be adjusted to improve sensitivity to the test material properties of interest, such as placing of the sensor conductors at a depth or circumferential position where cracks are expected to form. Alternatively, the test material properties can also be monitored with sensor conductors placed on the fastener shaft when the attachment configuration is designed to have clearance gaps between the fastener shaft and test material. This configuration minimizes fretting damage in the fastener hole and allows the sense conductors to monitor the test material properties within the hole. As another example, in many fasteners the bolts or fasteners are preloaded in an attempt to maintain consistency between joints and along the joint for multiple fastener systems. Loss in the loading of the fastener from the pre-load level can be monitored by using an embedded sensor or even with a scanning sensor. A state sensitive coating or fastener material can be used to enhance sensitivity to this fastener loading condition. When used for the detection of cracks around a fastener, this type of examination can be used to assess the airworthiness of an aircraft. This can be accomplished with electronics modules placed on-board the aircraft, like other instrumentation modules, or with off-board instrumentation after the aircraft has landed.

Figure 4:
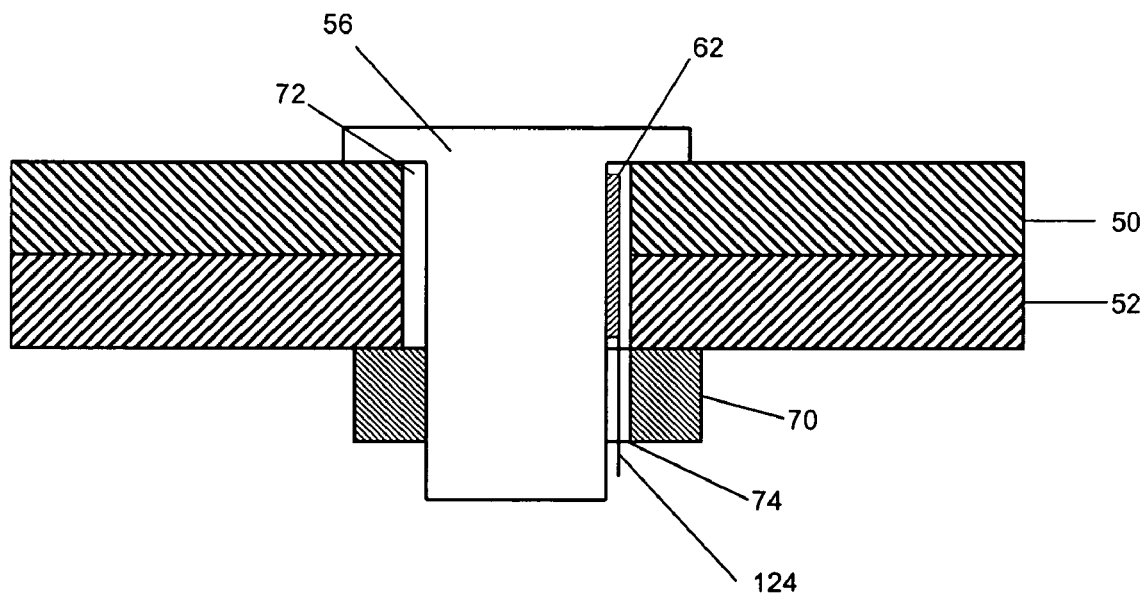
FIG. 4 shows a schematic diagram of a sensor mounted on the shaft of a fastener in the clearance gap between the fastener and material layer.

FIG. 4 shows an example embodiment where the sensor sleeve 62 is wrapped around the pin of a fastener 56. In this case, the nut 70 has an access channel or sealant groove through which the sensor leads 124 can be passed. While the sensor sleeve itself may have a protective layer to provide mechanical stability and strength, similar to the fastener material 58 of FIG. 1, when the fastener is intentionally sized smaller than the hole in the structure, the sensor sleeve may be placed in this clearance gap 72 between the fastener and structural material. This type of fastener design requires a substantial bearing surface so that a gap can be provided around the fastener pin or shaft and reduces the mechanical load on the sensor. Installation of the sensor is part of the installation of the fastener system. In this configuration, the sensor could be used to measure gap size and load. It could also be used for the detection and quantification of cracks and corrosion. Similarly, the sensor may be deposited directly onto the shaft of the fastener pin itself rather than as a sleeve. As described in U.S. patent application Ser. No. 10/937,105, filed on Sept. 8, 2004, the entire teachings of which are incorporated herein by reference, a state sensitive coating can be added to either the structure or the fastener to enhance sensitivity to the damage state of interest or to a usage state, such as load or temperature.

The use of a sensor embedded in a fastener can also be used as part of the manufacturing process. The installation tooling that installs the fastener can be modified to accommodate the insertion of a fastener, if necessary, and measurements of the sensor response after installation can verify the quality of the installation and the press-fit, as appropriate, and the alignment of the fastener in the material layers. For example, a recent study performed by Delta under FAA funding found that fasteners with cracks also tended to have the fastener misaligned with the hole. In some cases, this also led to the fastener head not being flush with the material surface. By using the sensors to measure the fastener response as part of the installation process, the likelihood of misalignment occurring can be reduced. Furthermore, the presence of unintentional damage from the installation procedure itself or inspections of the bolt hole eddy current may be found by measuring the response after the fastener is installed.

For insulating or semi-insulating materials, dielectric sensors which use an interrogating electric field are more suitable than inductive or magnetic field sensors for embedding in the fastener or adjacent materials. For these capacitive sensors, the dielectric properties of a material can often be described by two parameters, the permittivity and conductivity. The permittivity is a constitutive parameter that relates the displacement current density in the material to the applied electric field, whereas the conductivity applies to the conduction current density. The dielectric properties of materials vary significantly and can provide a means for characterization of the materials and their geometric properties such as size or layer thickness.

Figure 5:
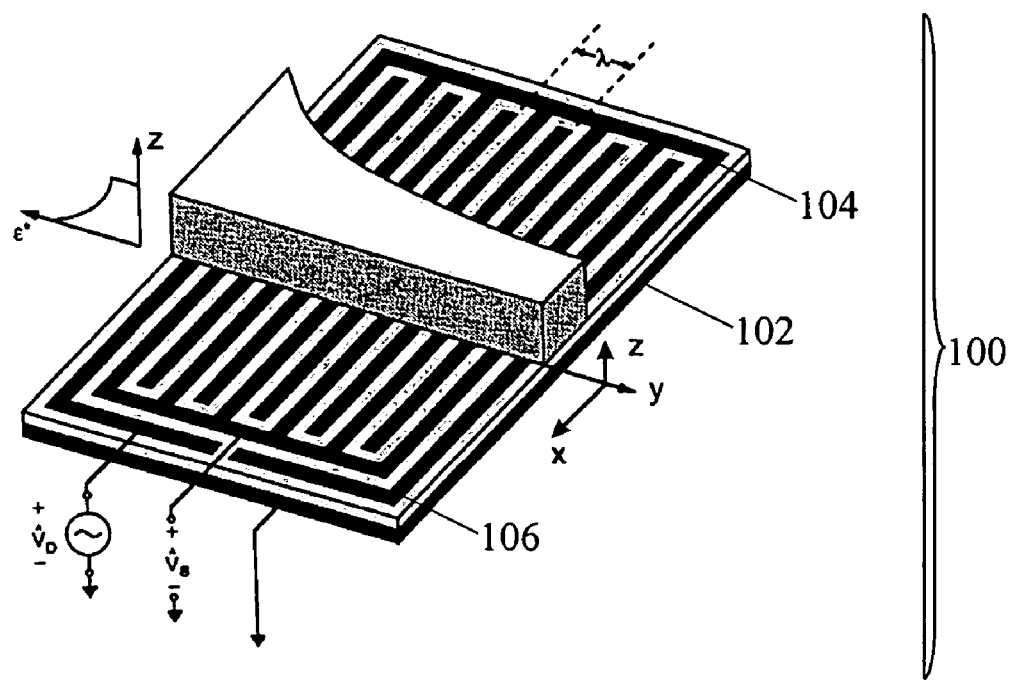
FIG. 5 shows a representative single wavelength interdigitated electrode dielectrometer with spatially periodic driven and sensing electrodes that can measure dielectric properties of the adjacent material.

A representative single sided sensor geometry is shown in FIG. 5. The application of a sinusoidally time varying potential of angular frequency $\omega=2\pi f$ results in the flow of a terminal current, whose magnitude and phase is dependent on the complex permittivity of the material. The capacitive sensor 100 has interdigitated electrodes as presented in U.S. Pat. Nos. 4,814,690, 6,380,747, 6,486,673 and 6,781,387 and in U.S. patent application Ser. No. 10/040,797, filed Jan. 7, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage $V_D$ while the other, 106, is connected to a high-impedance buffer used to measure the magnitude and phase of the floating potential $v_S$ or to a virtually grounded amplifier to measure the magnitude and phase of the terminal current. The periodicity of the electrode structure is denoted by the spatial wavelength $\lambda$. For layered media or materials having dielectric properties that vary with depth, the measured transadmittance between the drive and sense electrode, or the effective complex permittivity of the material, is a thickness and depth-weighted response of the dielectric properties of the various regions. Typical excitation frequencies range from 0.005 Hz for highly insulating materials to 10 MHz or higher for semiconducting materials.

For the interdigitated electrode dielectrometer of FIG. 5, the depth of penetration of the electric field into the material is proportional to the spatial wavelength of the periodic electrodes. The electric scalar potential in the materials above and below the sensor obeys Laplace's equation. In Cartesian coordinates with linear lossy dielectrics the potential can be written as an infinite series of sinusoidal Fourier modes of fundamental spatial wavelength $\lambda$ that decays into the medium the z direction. The periodic variation of electric potential along the surface in the y direction produces an exponentially decaying electric field that penetrates into the medium in the z direction. The depth of sensitivity is considered to be approximately $\frac{1}{3}$ of the fundamental spatial wavelength. This implies that small wavelength sensors will primarily respond to changes of material properties near the sensor-material interface, while larger wavelength sensors respond to changes farther from the sensor interface. Thus multiple wavelength sensors can be used to measure spatial profiles of dielectric properties; the necessary information to estimate multiple unknowns with these sensors can be accomplished via different spatial wavelengths or segmented fields.

In some cases, the fastener, fitting, bushing or other element of a joint or structure itself is a composite or has a layered construct. In this case, as with the embedded sensor sleeve 62 between the fastener 58 and insert 64 of FIG. 1, the sensor can be embedded between layers in the composite or layered construct. Both the sensing array and drive may simply be etched onto a carrier surface that permits embedding between layers in the composite fastener lay-up. It is also possible to weave the sensor windings, electrodes, or other electrical conductors into fabric layers or through the layered construct. In a particular embodiment, the fastener is a composite comprise of titanium alloy and graphite/epoxy layers and the electrical conductors for an inductive or eddy-current sensor is embedded into the composite. To enhance the composite electrical properties and enhance the observability of damage, nanoparticles, dopants, coatings, or wire mesh layers may also be embedded into the composites. For example, such wire meshes can be used to enhance composite properties for limiting damage from lightening strikes.

Figure 6:
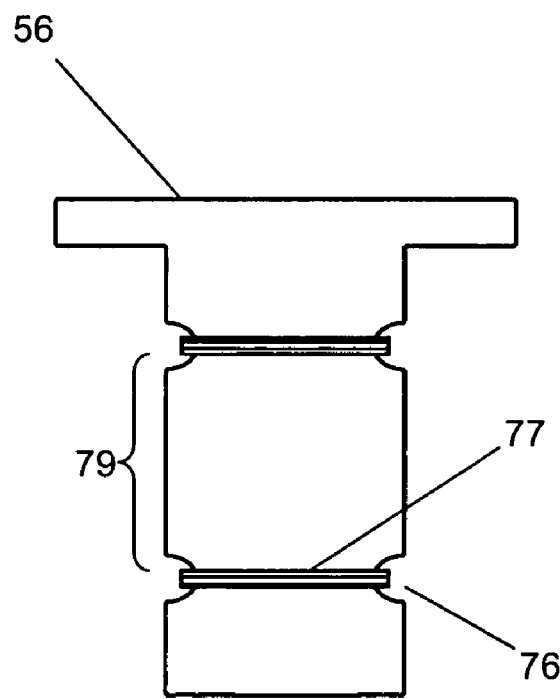
FIG. 6 shows a side view of a fastener containing wound coils.

FIG. 6 shows another example of a modified fastener design for monitoring the material condition. In this case, the fastener 56 has grooves 76 in the side of the fastener shaft for containing the conducting windings of inductive coils 77. Preferably, one coil is driven and the other acts as the sense coil to operate as a remote field eddy-current inspection. Alternatively, both coils could be operated as a drive with a sense element mounted under the head of the fastener in a "smart washer" format, with a sense located at the surface of the test material, or with an array of sense elements (for example shown in FIG. 3) also positioned inside the fastener or located on the surface of the fastener shaft. The use of washers containing sensor conductors is described in U.S. patent application Ser. No. 10/853,009, filed May 24, 2004, the entire teachings of which are hereby incorporated by reference. In another embodiment, the drive and sense coil windings may be placed adjacent to one another and pass through the same grooves. The grooves are deep enough so that the edges of the inductive coils are recessed or at most flush with the fastener shaft and permits insertion into standard size fastener holes in the material layers. The distance 79 between the inductive coils can be adjusted to the particular flaw or property depth of interest in the material layers. For example, if cracks are expected at the corner between material layers, then the coil positions can be adjusted so that they are adjacent to the material layer where the cracks will form. Alternatively, they can be positioned to straddle the interface between material layers.

Figure 7:
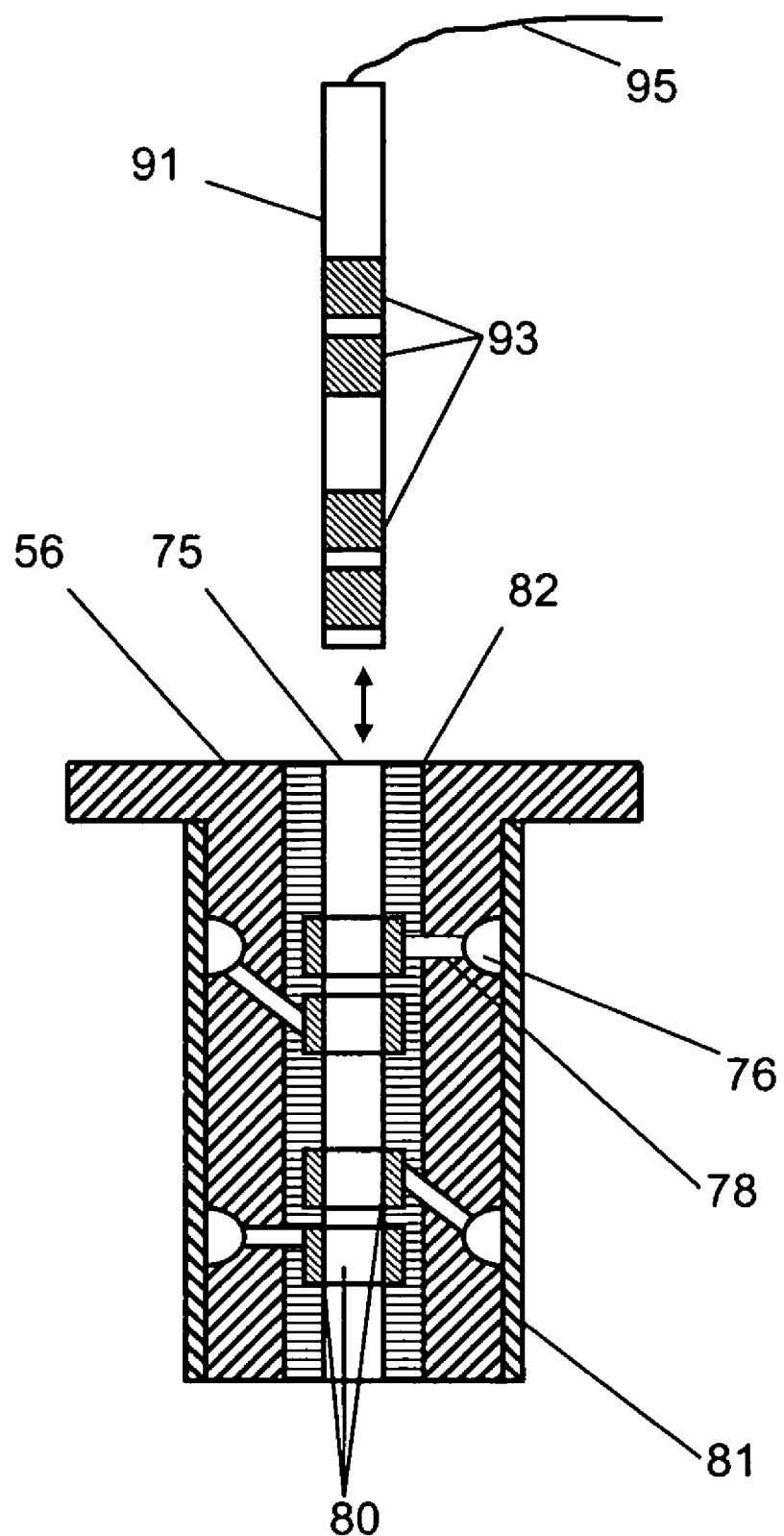
FIG. 7 shows a cross-sectional side view of a fastener adapted for containing wound coils.

FIG. 7 shows a cross-sectional view of the fastener design of FIG. 6 along with a connector 91. This cross-sectional view shows an access hole 75 through the center of the fastener and vias 78 through which the winding conductors can be fed. Electrical contact to the winding conductors is made through the bond pads 80 and isolated from the fastener itself, when it is fabricated from a conducting material, by an insulating or passivating layer 82. This design readily permits measurements on the fastener by inserting a connector probe 91 into the fastener access hole 75. The probe can be similar to commonly used audio jacks and allows for separate electrical contacts 93 to both ends of the inductive coils and through a cable 95 to measurement instrumentation. When not in use, a protective insert can be placed inside the access hole. Alternatively, the connections are made by removing a cap from the outside of the aircraft to enable easy connection. In addition, the access hole does not need to go all of the way through the fastener. It can be formed through the head or the bottom of the fastener, depending upon where it is more desirable to have access to the fastener for the measurement. Note that the protective sheath 81 of FIG. 7 may simply be placed around the fastener shaft to protect the sensor conductors. However, similar to FIG. 3, it may have sense elements deposited onto it as well.

As yet another alternative, the coil windings may be wrapped around the fastener in a spiral fashion, for example in the grooves of a threaded fastener. This type of spiral loop enables eddy-currents to be induced over the majority of the test material surface of interest. The sheath or sleeve of FIG. 7 could also be used to protect the sense conductors and vias can be made appropriately in the shaft of the fastener to permit convenient electrical connection to the sensor coil windings. The sleeve can also provide a uniform contact surface between the fastener with sleeve construct and the test material. It may also be in the form of a press-fit bushing, with the bushing material properties selected to enhance sensitivity to the test material state of interest, such as the presence of a crack or mechanical stress. Furthermore, a "grooveless" variation is possible, where multiple layers of insulation and sense conductors are deposited or sprayed onto the surface of the fastener shaft or even onto a second substrate, such as the protective sheath and wrapped around the fastener or insert.

Typically it is beneficial to convert the sense element response into more meaningful physical parameters associated with the test material, such as an electrical conductivity or magnetic permeability. In addition, if the sensor lift-off or proximity to the test material is determined, this provides self-diagnostic information about the state of the sensor, which is particularly useful for surface mounted sensor arrays where access to the sensor array may be limited. An efficient method for converting the sensor response into material or geometric properties is to use grid measurement methods. These methods map two known values, such as the magnitude and phase or real and imaginary parts of the sensor impedance, into the properties to be determined. The measurement grids are two-dimensional databases that can be visualized as "grids" that relate two measured parameters to two unknowns, such as the magnetic permeability (or electrical conductivity) and lift-off (where lift-off is defined as the proximity of the test material to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for near real-time measurements of the absolute electrical properties of the material and geometric parameters of interest. The database of the sensor responses can be generated prior to the data acquisition on the part itself, so that only table lookup and interpolation operations, which are relatively fast, needs to be performed after measurement data is acquired. Furthermore, grids can be generated for the individual elements in an array, such as those that couple to different segments of the magnetic field distribution, so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 8:
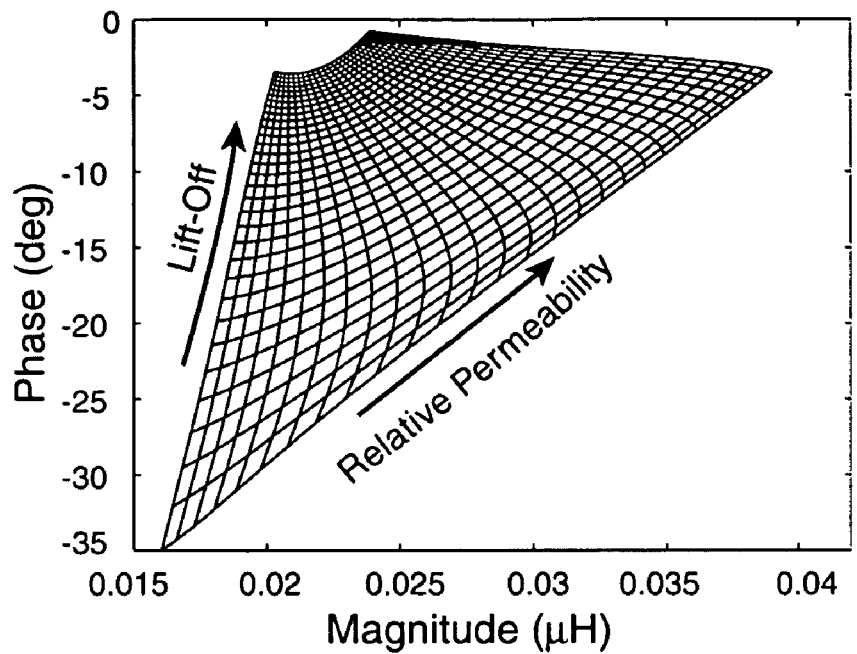
FIG. 8 shows a representative measurement grid relating the magnitude and phase of the sensor terminal impedance to the lift-off and magnetic permeability.
Figure 9:
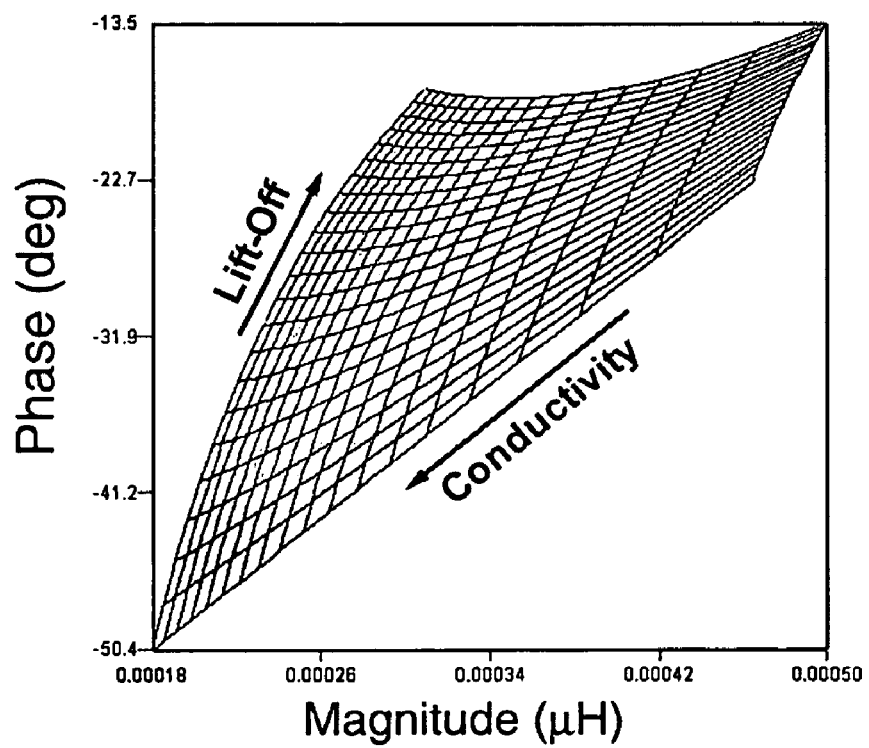
FIG. 9 shows a representative measurement grid relating the magnitude and phase of the sensor terminal impedance to the lift-off and electrical conductivity.

For ferromagnetic materials, such as most steels, a measurement grid can provide a conversion of raw data to magnetic permeability and lift-off. A representative measurement grid for ferromagnetic materials is illustrated in FIG. 8. A representative measurement grid for a low-conductivity non-magnetic alloy (e.g., titanium alloys, some superalloys, and austenitic stainless steels) is illustrated in FIG. 9. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest. The variation in the coating can be corrected at each point in the image to improve the measurement of permeability in the substrate for the purpose of imaging stresses. The effective property can also be a layer thickness, which is particularly suitable for coated systems. The effective property could also be some other estimated damage state, such as the dimension of a flaw or some indication of thermal damage for the material condition.

In addition to inductive coils, other types of sensing elements, such as Hall effect sensors, magnetoresistive sensors, SQUIDS, Barkhausen noise sensors, and giant magnetoresistive (GMR) devices, can also be used for the measurements. The use of GMR sensors for characterization of materials is described in more detail in U.S. patent application Ser. No. 10/045,650, filed Nov. 8, 2001, now U.S. Pat. No. 6,992,482, the entire teachings of which are incorporated herein by reference. Conventional eddy-current sensors are effective at examining near surface properties of materials but have a limited capability to examine deep material property variations. GMR sensors respond to magnetic fields directly, rather than through an induced response on sensing coils, which permits operation at low frequencies, even DC, and deeper penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations.

As an example demonstration of the capability to monitor disbond and delamination damage in graphite fiber composite structures, measurements were made during periodic loading with eddy-current sensor arrays mounted with an adhesive on multiple surfaces of a composite joint. Successful detection of damage in these composites using magnetic field sensors requires relatively high frequencies since the graphite fibers have relatively low electrical conductivity (approximately 0.058 MS/m, 0.1% IACS). Even at relatively high frequencies of 1 MHz to 40 MHz, the skin depth is relatively large so the penetration of the magnetic field into the composite material is limited by the geometry of the drive winding. For the sensor arrays based on the geometry of FIG. 1, this corresponds to the Laplacian limit and sensitivity to deep flaws requires the use of relatively long spatial wavelengths. Initially, the conductivity of the graphite fiber composite comprising the joint and base of the specimens was measured after and a calibration in air and with a shunt in air. For comparison, the conductivity of a bar of titanium alloy was also measured. Data for each was acquired over a range of lift-offs in 0.005 in. increments. Based on these preliminary air calibration measurements, an average conductivity of 0.015% IACS was used as the electrical conductivity of the carbon composite. This bulk conductivity is within about 10 percent of the expected fiber conductivity mentioned above.

Based on prior testing experience, it was expected that the specimens could withstand a load of approximately 200 lbf. The load cycles were applied incrementally, e.g., for the first load cycle of the first specimen, data was acquired at loads of 0, 50, 100, 125, 142 (150 was the targeted load), and 0 lbf. It was intended that the load would be increased in predetermined steps. However, if the specimen emitted an audible indication of individual fiber failure, the crosshead was stopped and data acquired. Often, with the specimen held at a constant displacement, load would continue to shed as fibers failed. Data would then be acquired through time at a set displacement and variable, decreasing load. Occasionally, the maximum load for a cycle was reached several times prior to unloading. These tests were not strictly fatigue tests but rather a few loading and unloading cycles intended to impart damage to the joint structure.

Figure 10:
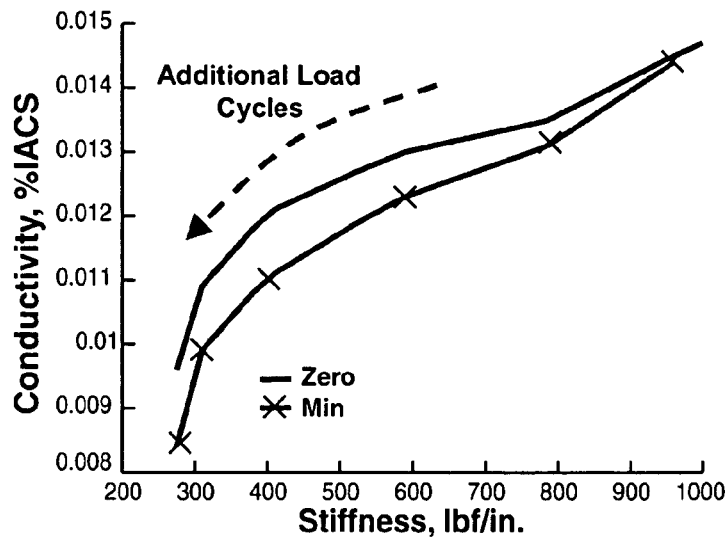
FIG. 10 shows a plot of the effective conductivity variation with stiffness for a composite joint.

As damage accumulated within loading cycles and the delamination extends through the joint, away from the centerline, the response from the neighboring channels of the sensor array decreased in both effective lift-off and conductivity. This decrease in the effective properties with extension of the delamination continued throughout the duration of the tests. A plot of this behavior captures the relationship between the measured property and the accumulated damage via the reduction in the stiffness of the joint. FIG. 10 shows that a strong correlation exists between the reduction in the property and the reduction in the stiffness of the joint. The data for a loading cycle were taken at zero load or the minimum for that cycle. The stiffness was taken as the average of the unloading and loading portion of neighboring cycles between 50 and 100 pounds (except for the initial curve, where the stiffness was determined solely by the first load ramp). Note that the presence of the delamination was noticeable in either the unloaded or loaded state.

Figure 11:
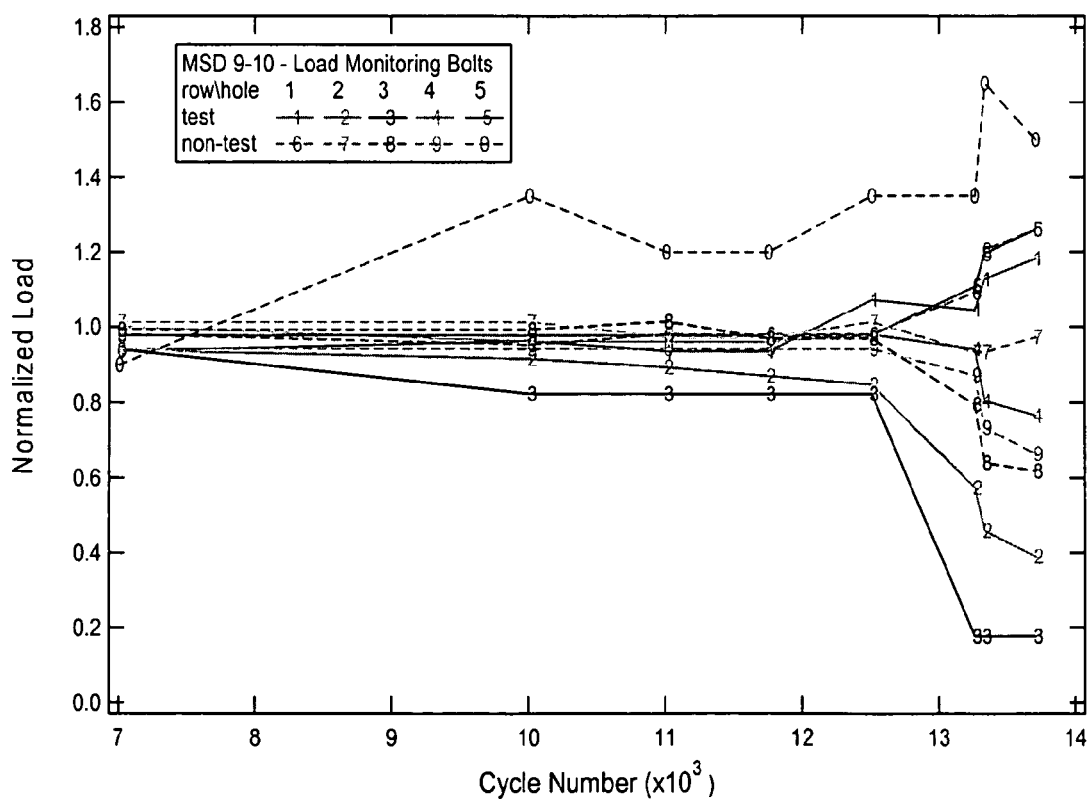
FIG. 11 shows a plot of the fastener load redistribution with fatigue damage in a mechanically fastened joint.

As another example demonstration, a network of embedded linear eddy-current sensor arrays has also been used for the monitoring of load redistribution in a generic, mechanically fastened lap joint. In this case, the sensors were mounted inside hollow fasteners and monitored as the joint was cyclically loaded. Tests were performed on specimens having two rows of fasteners with five fasteners in each row. One row of fasteners, the test row, were precracked with different cracks emanating from the fastener holes as part of a multi-site fatigue damage test while the other row of fasteners, the non-test row, did not have any precrack damage. In this case, the effective permeability or each fastener was measured and correlated with the load with the fastener itself. This permeability was then used to determine the load on each fastener. FIG. 11 shows an example plot of the normalized load (relative to the initial load) during the fatigue test. In this case, the test was stopped when the joint failed, at approximately 13,800 cycles. Near the end of the fatigue test, as the cracks in the joint continued to grow, the load distribution on the fasteners also changed.

Figure 12:
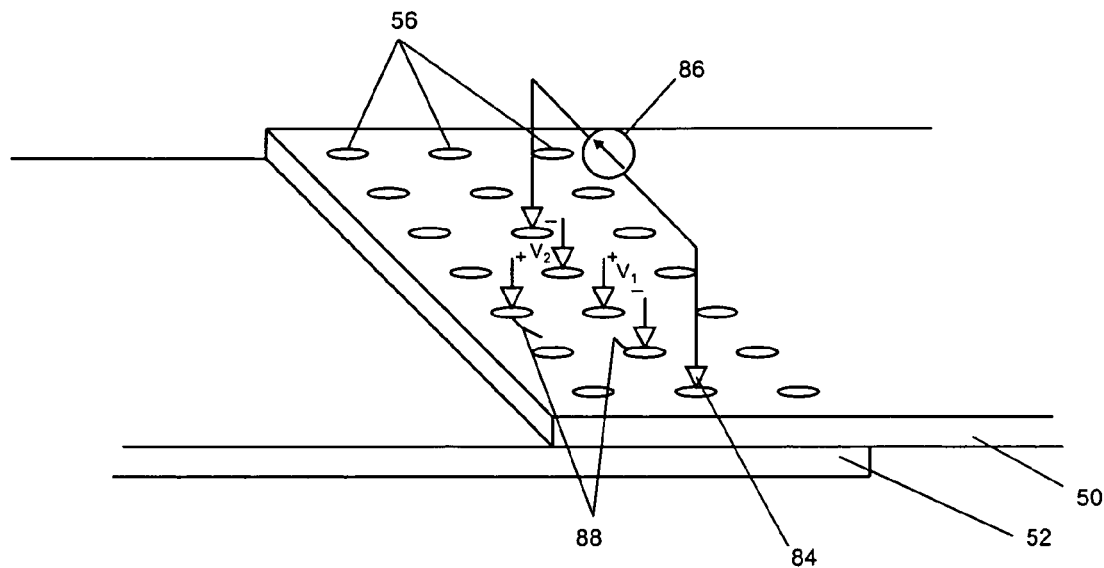
FIG. 12 shows a schematic diagram for a lapjoint containing multiple fasteners and probe connections to some of the fasteners.

In situations where multiple fasteners are used to join the material layers, the fasteners themselves can be used as part of a fastener sensing system for a "macro" sensing method. As shown in FIG. 12, numerous fasteners 56 are used to attach two material layers 50 and 52. Probes 84 are placed in contact with the fastener heads and used to insert electrical current into the material structure from a current source 86. The electric potential or voltage between pairs of fasteners is then measured and used to assess the material condition, such as the presence of cracks 86 that may be hidden beneath paint layers or in lower test material layers. The electric potential can be measured directly from the drive probes but this is usually of limited benefit because of variations in the contact resistance between the probes and the fastener heads. Alternatively, separate probes can be placed in electrical contact with other sense fasteners. For these sensor probes, the dependence on contact resistance is greatly reduced since only the relative potentials are to be measured. These sense fasteners may be collinear with the driven fasteners or some other combination of fasteners can be used. Preferably, both sense fasteners are positioned between the driven fasteners.

This type of measurement with the fasteners is similar to the conventional four-point probe measurement, except that the fasteners themselves are used as part of the measurement procedure. Models developed for conventional four-point probe responses to test material properties and electrode position placement, such as analytical models described by Bowler (2006) and finite element or boundary element numerical models, can be adapted to account for the fastener effects and insertion of current throughout the material volume. The resulting sensor responses can then be used to develop measurement grids as described above for converting the sensor responses into test material properties.

Figure 14:
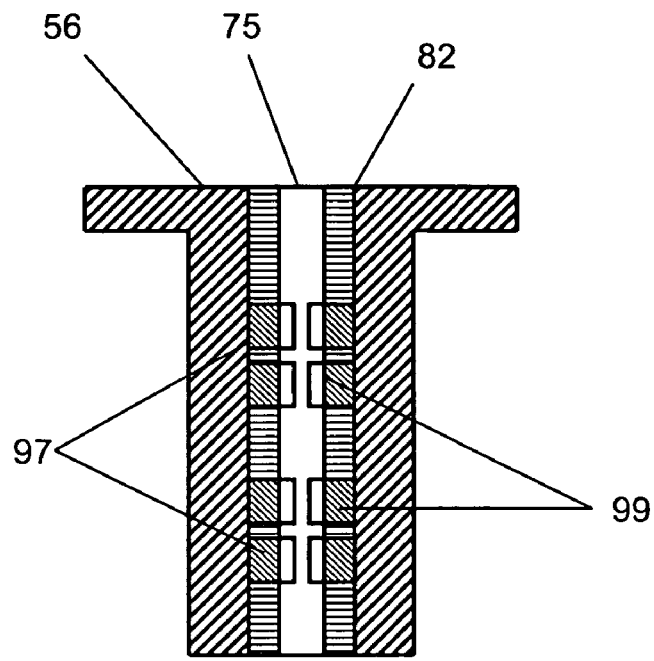
FIG. 14 shows a cross-sectional side view of a fastener having a several electrical contacts.

Of course, the potential in-between the fasteners can also be measured so that the voltage distribution at multiple positions along the surface can be used to provide an assessment of the material state or condition. These measurements could use probes that make electrical contact with the surface, with magnetic field sensor positioned over the surface, such as inductive loops or coils or magnetoresistive sensors, or with capacitive sensors positioned over the material surface. In a similar fashion, using a fastener like that shown in FIG. 14, contacts 97 can be placed on the inside of the fastener for the drive conductor and can be used to inject electrical current into the fastener and test material. Additional contacts 99 can be used for the sense conductors so that the voltage difference on the these other two contacts can be used to measure a test material response as a four-point potential drop measurement. These contacts can be aligned linearly along the axis of the fastener and/or located circumferentially around the fastener.

This type of measurement is well-suited to the monitoring of damage in graphite-epoxy composite materials as well as metals. Measurements of the effective electrical conductivity between relevant fasteners can then provide an indication of damage, such as the presence of cracks, disbonds, delaminations between composite layers, fiber cracking, or thermally induced damage. The sensor response can also be obtained at multiple states of a load, temperature, or other measurable variable. These multiple state measurements can provide complementary information about the damage or defect state.

As a variation of the potential drop sensor, similar to the eddy-current sensor of FIG. 2, the current can be injected and withdrawn through neighboring fasteners in a periodic fashion. Then the contact voltage measurement is made between fasteners (e.g., a DC potential drop or AC potential drop method) or a magnetic field measurement is made (inductive coils, Hall effect probes, or magnetoresistive sensors).

Figure 13:
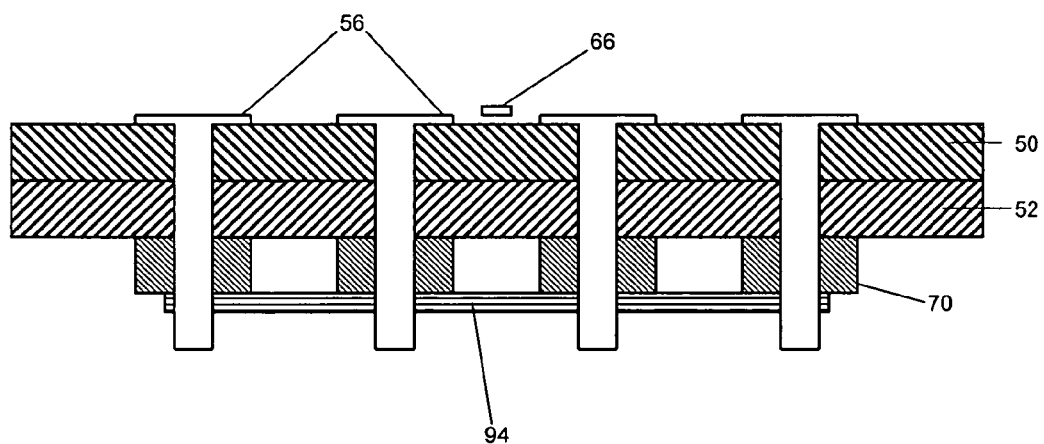
FIG. 13 shows a cross-sectional view of two material layers joined by multiple fasteners with a cross-connection between the fasteners.

As another variation, no electrical connection is required between the composite and the metal fastener. As shown in FIG. 13, current or flux is carried through the fastener with linking means 94 to close the electric current or magnetic circuit. In such a configuration, a sense element 66 can be scanned over the material surface or permanently mounted to the material surface to monitor the damage progression or usage states. This configuration uses the fasteners as a means to enhance the monitoring of composite conductivity through connection to fasteners using the fasteners to either insert current into the composite or to insert an interrogating field such as a magnetic field. As an example, this can be used to monitor the properties of a stringer in an aircraft. The stringer can be electrically isolated, except through the fastener contacts, for example by using glass fiber composite layers, so that the current is inserted through the stringer.

As yet another variation of the multiple probe current insertion approach, voltage pickup probes are located at different circumferential positions around the shaft of the fastener. This enables the location of crack or damage position and coverage of the full circumference of the fastener. As part of the installation, the fastener installation tooling may enable insertion without electrical contact and then using a rotational motion or other means may engage the fastener or electrical contacts in the fastener, possibly with mechanical stress, to maintain good electrical continuity. This provides greater sensitivity for local damage detection than the use of fasteners for the voltage pickup, at the expense of narrower examination areas. In one such embodiment, an apparatus similar to that shown in FIG. 1 or FIG. 7 can be used with embedded potential drop sensors.

Numerous other variations on these methods are also possible. For example, the fastener material itself (58 in FIG. 1) could be made of a material whose properties, such as the magnetic permeability or electrical conductivity, change with fatigue damage, stress or temperature. This type of fastener could then be used for cumulative life monitoring. A representative material would be a stainless steel alloy, such as a 304 stainless steel, that becomes significantly magnetic with fatigue cycling. The fastener could also be made of a material whose properties change with stress, such as a steel, titanium alloy, or a cobalt containing alloy, which permits load monitoring on the structure through the load on the fasteners. Similar approaches can also be used for the monitoring of bushings and the properties of the adjacent materials. Furthermore, the embedding of sensor conductors into composites for fasteners can be extended to composites used for structural elements. An example is the embedding of capacitive or dielectric sensors into GLARE (which has alternating metallic and insulating layers), glass fiber, or ceramic matrix composite constructs so that the dielectric properties of the composite can be monitored. In a specific embodiment, electrical connections are made to some of the individual metal layers in a GLARE composite so that the metal layers are used as the electrodes of the dielectrometer to interrogate the glass fiber composite layers.

While the inventions have been particularly shown and described with reference to preferred embodiments thereof, it will be understood to those skilled in the art that various changes in form and details may be made therein without departing from the spirit and scope of the invention as defined by the appended claims.

References Incorporated by Reference in their Entirety:
1. Bowler, N. (2006), "Theory of Four-Point Direct-Current Potential Drop Measurements on a Metal Plate," Research in Nondestructive Evaluation, vol. 17, pages 29-48.
2. Navy Phase I Proposal, titled "In-situ projected field and near surface sensors for direct condition monitoring of engine hot section components," Topic #N06-T011, dated Apr. 13, 2006.

What is claimed is:

1. A method for monitoring a test material around a fastener comprising:
   mounting a fastener into a test material, the fastener having integrated conductors, the integrated conductors being embedded in a surface of the fastener;
   driving the conductors with an electric signal to create an interrogating field within the test material; and
   measuring a response with at least one other conductor to measure the test material.

2. The method as claimed in claim 1 wherein the integrated conductor is driven with a current and the voltage is measured on a second conductor.

3. The method as claimed in claim 2 wherein the second conductor further comprises multiple sense conductors, each having the form of a simple loop, placed in a circumferential configuration along a surface of the test material outside of the fastener hole, with a voltage across each sensor conductor measured.

4. The method as claimed in claim 2 wherein electrical connections to the conductor are made through a head of the fastener.

5. The method as claimed in claim 1 further comprising at least one sense conductor integrated into the fastener and located in the fastener hole, with the fastener and conductors forming a single construct for ease of installation.

6. The method as claimed in claim 1 further comprising the fastener having a channel to provide access to at least one conductor integrated into the fastener, and inserting a connector into the channel to contact a conductor.

7. The method as claimed in claim 6 further comprising the channel being a cylindrical hole and the connector having the form of a cylindrical plug that can be inserted into the fastener from one side.

8. The method as claimed in claim 1 wherein the fastener further comprises an indicator layer that enhances sensitivity to the test material condition.

9. The method as claimed in claim 1 wherein the interrogating field is magnetic.

10. The method as claimed in claim 1 wherein the interrogating field is electric.

11. A method for detecting the state of a test material comprising:
   mounting a fastener within a test material, the fastener including an integrated drive conductor, the integrated drive conductor being embedded in a surface of the fastener;
   driving the conductor with a current to produce a magnetic field that induces eddy-currents in the test material;
   locating a sense conductor near the test material;
   measuring a response of the sense conductor to the magnetic field; and
   using the response to determine a state of the test material.

12. The method as claimed in claim 11 further comprising multiple sense conductors, each having the form of a simple loop, placed in a circumferential configuration along a surface of the test material outside of the fastener hole, with a voltage across each sensor conductor measured.

13. The method as claimed in claim 11 further comprising at least one sense conductor integrated into the fastener and located in the fastener hole, with the fastener and conductors forming a single construct for ease of installation.

14. The method as claimed in claim 11 further comprising the fastener having a channel to provide access to at least one conductor integrated into the fastener, and inserting a connector into the channel to contact a conductor.

15. The method as claimed in claim 14 further comprising the channel being a cylindrical hole and the connector having the form of a cylindrical plug that can be inserted into the fastener from one side.

16. The method as claimed in claim 11 further comprising:
   the state being stress;
   providing a correlation between sense conductor response and stress; and
   using the correlation to determine the stress from the response.

17. The method as claimed in claim 11 further comprising the fastener having a sensitive material layer that enhances the sensitivity of the response to the state of interest.

18. The method as claimed in claim 17 wherein the sensitive material layer is in the form of a coating.

19. The method as claimed in claim 17 wherein the sensitive material has an electrical property that varies with cumulative damage.

20. The method as claimed in claim 11 further comprising at least one conductor being deposited onto the fastener, including an insulating layer between the conductor and the fastener material and a second insulating layer between the conductor and the test material.

21. The method as claimed in claim 11 further comprising the drive conductor forming a solenoid around the fastener shaft.

22. The method as claimed in claim 11 further comprising the state being damage in the form of a crack.

23. The method as claimed in claim 22 wherein the fastener is in an aircraft.

24. The method as claimed in claim 11 wherein the sense conductor is in the form of a washer.

25. The method as claimed in claim 11 further comprising the fastener having a sleeve placed around the fastener.

26. The method as claimed in claim 25 wherein the sleeve provides protection of the conductors and a uniform contact surface between the test material and fastener with sleeve construct.

27. The method as claimed in claim 25 wherein the sleeve is in the form of a press-fit bushing and the bushing material is selected to enhance sensitivity to the state of interest.

28. The method as claimed in claim 11 further comprising the drive conductor having two contact points for applying electrical current and two other sense contact points for measuring a voltage difference.

29. The method as claimed in claim 28 further comprising the contact points are located in a line along the axis of the fastener.

30. The method as claimed in claim 28 further comprising one or more additional drive conductor and sense contact points, the additional contact points located at a different circumferential position around the fastener.

31. The method as claimed in claim 11 further comprising the state being temperature, converting the sense response into an electrical property, and using the electrical property to determine the temperature.

32. A method for monitoring a test material around a fastener comprising:
mounting a fastener into a test material, the fastener having integrated conductors;
inserting a cylindrical plug in a channel of the fastener to provide access to the integrated conductors;
driving the conductors with an electric signal to create an interrogating field within the test material;
measuring a response with at least one other conductor to measure the test material.

33. A method for detecting the state of a test material comprising:
mounting a fastener within a test material, the fastener including an integrated drive conductor;
accessing the integrated drive conductor through two contact points located on the integrated drive conductor and in a line along an axis of the fastener;
driving the conductor with a current to produce a magnetic field that induces eddy-currents in the test material;
locating a sense conductor near the test material;
measuring a response of the sense conductor to the magnetic field; and
using the response to determine a state of the test material.

* * * * *